US009572858B2

(12) United States Patent
Kim

(10) Patent No.: US 9,572,858 B2
(45) Date of Patent: *Feb. 21, 2017

(54) COMPOSITION FOR TREATING AND PREVENTING BENIGN PROSTATIC HYPERPLASIA

(71) Applicant: GemVax & KAEL Co., Ltd., Daejeon (KR)

(72) Inventor: Sang Jae Kim, Seoul (KR)

(73) Assignee: GemVax & KAEL Co., Ltd., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/136,353

(22) Filed: Apr. 22, 2016

(65) Prior Publication Data

US 2016/0250279 A1    Sep. 1, 2016

Related U.S. Application Data

(63) Continuation of application No. PCT/KR2014/010035, filed on Oct. 23, 2014.

(30) Foreign Application Priority Data

Oct. 23, 2013 (KR) .................. 10-2013-0126666

(51) Int. Cl.
 *A61K 38/10* (2006.01)
 *A61K 9/00* (2006.01)
 *A61K 9/19* (2006.01)
 *A61K 38/45* (2006.01)

(52) U.S. Cl.
 CPC ............ *A61K 38/10* (2013.01); *A61K 9/0056* (2013.01); *A61K 9/19* (2013.01); *A61K 38/45* (2013.01); *C12Y 207/07049* (2013.01)

(58) Field of Classification Search
 None
 See application file for complete search history.

(56) References Cited

U.S. PATENT DOCUMENTS

| | | | |
|---|---|---|---|
| 6,967,211 B2 | 11/2005 | Inoue | |
| 7,794,723 B2 | 9/2010 | Gaudernack et al. | |
| 8,828,403 B2 | 9/2014 | Filaci et al. | |
| 8,933,197 B2 | 1/2015 | Stemmer et al. | |
| 9,023,987 B2 | 5/2015 | Chung et al. | |
| 2006/0106196 A1 | 5/2006 | Gaudernack et al. | |
| 2007/0190561 A1 | 8/2007 | Morin et al. | |
| 2009/0136917 A1 | 5/2009 | Szalay et al. | |
| 2009/0186802 A1 | 7/2009 | Alluis et al. | |
| 2011/0150873 A1 | 6/2011 | Grainger | |
| 2011/0183925 A1 | 7/2011 | Sato et al. | |
| 2012/0065124 A1 | 3/2012 | Morishita et al. | |
| 2013/0129760 A1 | 5/2013 | Gaudernack et al. | |
| 2015/0099692 A1 | 4/2015 | Kim et al. | |
| 2015/0175978 A1 | 6/2015 | Kim | |
| 2015/0307859 A1 | 10/2015 | Kim | |
| 2015/0343095 A1 | 12/2015 | Kim | |
| 2015/0353903 A1 | 12/2015 | Kim | |
| 2016/0002613 A1 | 1/2016 | Kim | |
| 2016/0008438 A1 | 1/2016 | Kim | |

FOREIGN PATENT DOCUMENTS

| | | |
|---|---|---|
| EP | 1020190 A3 | 10/2000 |
| EP | 1093381 B2 | 7/2009 |
| EP | 1817337 B1 | 1/2011 |
| JP | 2010252810 A | 11/2010 |
| KR | 20010012613 A | 2/2001 |
| KR | 20010020601 A | 3/2001 |
| KR | 20040015087 A | 2/2004 |
| KR | 20040045400 A | 6/2004 |
| KR | 20050020987 A | 3/2005 |
| KR | 20050040517 A | 5/2005 |
| KR | 20060109903 A | 10/2006 |
| KR | 20070083218 A | 8/2007 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120087885 A | 8/2012 |
| WO | WO-0002581 A1 | 1/2000 |
| WO | WO-2010003520 A2 | 1/2010 |
| WO | WO-2010012850 A1 | 2/2010 |
| WO | WO-2011101173 A1 | 8/2011 |
| WO | WO-2011150494 A1 | 12/2011 |
| WO | WO-2013135266 A1 | 9/2013 |
| WO | WO-2013167574 A1 | 11/2013 |
| WO | WO-2013169060 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014171792 A1 | 10/2014 |
| WO | WO-2014196841 A1 | 12/2014 |
| WO | WO-2014204281 A1 | 12/2014 |

OTHER PUBLICATIONS

Shaw et al. ("Current status of GV1001 and other telomerase vaccination strategies in the treatment of cancer," Expert Rev. Vaccines, 2010, vol. 9, pp. 1007-1016).*

(Continued)

*Primary Examiner* — Christina Bradley
(74) *Attorney, Agent, or Firm* — Sterne, Kessler, Goldstein & Fox P.L.L.C.

(57) ABSTRACT

The present invention relates to a composition for treating and preventing benign prostatic hyperplasia, and a method for treating benign prostatic hyperplasia using same. More specifically, the present invention relates to a composition comprising telomerase-derived peptides for effectively treating and preventing benign prostatic hyperplasia and a method for treating benign prostatic hyperplasia using same. The composition comprising the peptide according to the present invention exhibits excellent effectiveness in treating and preventing benign prostatic hyperplasia.

17 Claims, 15 Drawing Sheets

(56) References Cited

OTHER PUBLICATIONS

Morishita et al. ("Is the oral route possible for peptide and protein drug delivery?" Drug Discovery Today 2006, vol. 11, pp. 905-910).*
NIDDK (www.niddk.nih.gov/health-information/health-topics/urologic-disease/benign-prostatic-hyperplasia-bph/Pages/facts.aspx, downloaded Jul. 28, 2016).*
Dementia from Merck Manual, accessed on Jul. 29, 2009, pp. 1-17.
Mattson, M.P., "Pathways Towards and Away From Alzheimer's Disease," Nature 430(7000):631-639, Nature Publishing Group, England (2004).
Perez, R.G., et al., "The Beta-amyloid Precursor Protein of Alzheimer's Disease Enhances Neuron Viablity and Modulates Neuronal Polarity," The Journal of Neuroscience 17(24):9407-9414, Society for Neuroscience, United Sates (1997).
Rheumatoid Arthritis from Merck Manual, accessed on Apr. 21, 2016, pp. 1-18.
Schenk, D., et al., "Immunization with Amyloid-beta Attenuates Alzheimer-disease-like Pathology in the PDAPP Mouse," Nature 400(6740):173-177, Nature Publishing Group, England (1999).
Altschul, S.F., et al., "Basic Local Alignment Search Tool," Journal of Molecular Biology 215(3):403-410, Elsevier, England (1990).
Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).
Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).
Brandenburg, K., et al., "Peptide-based Treatment of Sepsis," Applied Microbiology and Biotechnology 90(3):799-808, Springer International, Germany (2011).
Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, The Association, United States (2011).
Cho, Y.J., "GemVax & Kael (082270)," Hana Daetoo Securities, Company Report, Sep. 10, 2012, 8 pages.
Choi, S.G., "Recent Advances in Cancer Cachexia," Journal of Korean Oncology Nursing 11(1):20-25 (2011).
Co-pending U.S. Appl. No. 14/413,732, inventor Sang Jae Kim, filed Jul. 11, 2013 (Not Published).
Co-pending U.S. Appl. No. 14/896,358, inventor Sang Jae Kim, filed Dec. 4, 2015 (Not Published).
Co-pending U.S. Appl. No. 14/899,746, inventor Sang Jae Kim, filed Apr. 12, 2015 (Not Published).
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
Dinarello, C.A., "Interleukin-1 in the Pathogenesis and Treatment of Inflammatory Diseases," Blood 117(14):3720-3732, American Society of Hematology, United States (2011).
Engineer, D.R. and Garcia, J.M., "Leptin in Anorexia and Cachexia Syndrome," International Journal of Peptides 2012:Article ID 287457, Hindawi Publishing Corporation, United States (2012).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fujii, H., et al., "Telomerase Insufficiency in Rheumatoid Arthritis," Proceedings of the National Academy of Sciences USA 106(11):4360-4365, National Academy of Sciences, United States (2009).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Heitz, F., et al., "Twenty Years of Cell-Penetrating Peptides: From Molecular Mechanisms to Therapeutics," British Journal of Pharmacology 157(2):195-206, Wiley, England (2009).
Hse, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor & Francis, United States (2012).
International Preliminary Report on Patentability for International Application No. PCT/EP2013/059460, International Bureau of WIPO, Switzerland, mailed Nov. 11, 2014, 5 pages.
International Preliminary Report on Patentability for International Application No. PCT/KR2013/004145, The International Bureau of WIPO, Switzerland, issued Nov. 11, 2014, 14 pages.
International Preliminary Report on Patentability for International Application No. PCT/KR2013/004176, The International Bureau of WIPO, Switzerland, issued Nov. 11, 2014, 14pages.
International Preliminary Report on Patentability for International Application No. PCT/KR2013/006218, The International Bureau of WIPO, Switzerland, issued Jan. 13, 2015, 27 pages.
International Preliminary Report on Patentability for International Application No. PCT/KR2013/008438, The International Bureau of WIPO, Switzerland, issued Mar. 24, 2015, 10 pages.
International Preliminary Report on Patentability for International Application No. PCT/KR2013/008445, The International Bureau of WIPO, Switzerland, issued Mar. 24, 2015, 13 pages.
International Preliminary Report on Patentability for International Application No. PCT/KR2014/003425, The International Bureau of WIPO, Switzerland, mailed Oct. 20, 2015, 14 pages.
International Preliminary Report on Patentability for International Application No. PCT/KR2014/005031, The International Bureau of WIPO, Switzerland, issued Dec. 8, 2015, 8 pages.
International Preliminary Report on Patentability for International Application No. PCT/KR2014/005508, The International Bureau of WIPO, Switzerland, mailed Jan. 5, 2016, 14 pages.
International Preliminary Report on Patentability for International Patent Application No. PCT/KR2013/004156, The International Bureau of WIPO, Geneva, Switzerland, mailed Nov. 11, 2014, 15 pages.
International Search Report for International Application No. PCT/KR2014/003425, Korean Intellectual Property Office, Republic of Korea, mailed Jul. 21, 2014, 8 pages.
International Search Report for International Application No. PCT/EP2013/059460, European Patent Office, Netherlands, mailed Jul. 3, 2013, 5 pages.
International Search Report for International Application No. PCT/KR2013/004145, Korean Intellectual Property Office, Republic of Korea, mailed Aug. 14, 2013, 10 pages.
International Search Report for International Application No. PCT/KR2013/004176, Korean Intellectual Property Office, Republic of Korea, mailed Aug. 6, 2013, 10 pages.
International Search Report for International Application No. PCT/KR2013/006218, Korean Intellectual Property Office, Republic of Korea, mailed Sep. 26, 2013, 8 pages.
International Search Report for International Application No. PCT/KR2013/008438, Korean Intellectual Property Office, Republic of Korea, mailed Dec. 23, 2013, 8 pages.

(56) References Cited

OTHER PUBLICATIONS

International Search Report for International Application No. PCT/KR2013/008445, Korean Intellectual Property Office, Republic of Korea, mailed Dec. 23, 2013, 10 pages.

International Search Report for International Application No. PCT/KR2014/005031, Korean Intellectual Property Office, Republic of Korea, mailed Sep. 22, 2014, 6 pages.

International Search Report for International Application No. PCT/KR2014/005508, Korean Intellectual Property Office, Republic of Korea, mailed Oct. 14, 2014, 8 pages.

International Search Report for International Application No. PCT/KR2014/010035, Korean Intellectual Property Office, Republic of Korea, mailed Feb. 2, 2015, 8 pages.

International Search Report for International Patent Application No. PCT/KR2013/004156.

International Search Report for International Application No. PCT/KR2013/008459, Korean Intellectual Property Office, Republic of Korea, mailed Dec. 23, 2013, 8 pages.

Kern, K.A. and Norton, J.A., "Cancer Cachexia," Journal of Parenteral and Enteral Nutrition 12(3):286-298, Sage Publications, United States (1988).

Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).

Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).

Kyte, J.A., "Cancer Vaccination with Telomerase Peptide GV1001," Expert Opinion on Investigational Drugs 18(5):687-694, Taylor & Francis, England (2009).

Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).

Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).

Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).

Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).

Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).

McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).

Modica-Napolitano, J.S. and Singh, K.K., "Mitochondria as Targets for Detection and Treatment of Cancer," Expert Reviews in Molecular Medicine 4(9):1-19, Cambridge University Press, England (2002).

Myers, L.K., et al., "Collagen-Induced Arthritis, an Animal Model of Autoimmunity," Life Sciences 61(19):1861-1878, Elsevier, Netherlands (1997).

National Horizon Scanning Centre News on Emerging Technologies in Healthcare, GV1001 for Advanced and/or Metastatic Pancreatic Cancer, Published Apr. 2008.

NCBI, Reference Sequence: XP_003776612.1 (Jul. 17, 2012).

Novina, C.D. and Sharp, P.A., "The RNAi Revolution," Nature 430(6996):161-164, Nature Publishing Group, England (2004).

Oh, H., et al., "Telomerase Reverse Transcriptase Promotes Cardiac Muscle Cell Proliferation, Hypertrophy, and Survival," Proceedings of the National Academy of Sciences 98(18): 10308-10313, National Academy of Sciences, United States (2001).

Pearson, W.R. and Lipman, D.J., "Improved Tools for Biological Sequence Comparison," Proceedings of the National Academy of Sciences USA 85(8):2444-2448, National Academy of Sciences, United States (1988).

Rana, T.M., "Illuminating the Silence: Understanding the Structure and Function of Small RNAs," Nature Reviews. Molecular Cell Biology 8(1):23-36, Nature Publishing Group, England (2007).

Roubenoff, R., et al., "Adjuvant Arthritis as a Model of Inflammatory Cachexia," Arthritis and Rheumatism 40(3):534-539, Wiley-Blackwell, United States (1997).

Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).

Shay, J.W., and Wright, W.E., "Telomerase Therapeutics for Cancer: Challenges and New Directions," Nature Reviews. Drug Discovery 5(7):577-584, Nature Publishing Group, England (2006).

Smith, D.B. and Johnson, K.S., "Single-step Purification of Polypeptides Expressed in *Escherichia coli* as Fusions with Glutathione S-transferase," Gene 67(1):31-40, Elsevier, Netherlands (1988).

Smith, T.F. and Waterman, M.S., "Comparison of Biosequences," Advances in Applied Mathematics 2(4):482-489, Academic Press, Inc., United States (1981).

Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.

Stevenson, C.L., "Advances in Peptide Pharmaceuticals," Current Pharmaceutical Biotechnology 10(1):122-137, Bentham Science Publishers, United Arab Emirates (2009).

Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).

Thompson, J.D., et al., "Clustal W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).

Tisdale, M.J., "Mechanisms of Cancer Cachexia," Physiological Reviews 89(2):381-410, American Physiological Society, United States (2009).

Tomari Y. and Zamore, P.D., "Perspective: Machines for RNAi," Genes and Development 19(5):517-529, Cold Spring Harbor Laboratory Press, United States (2005).

Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).

Vennela, B., et al., "Current and Future Strategies for Therapy of Pancreatic Cancer," International Journal of Research in Pharmacy and Medicine 2(3):728-740 (2012).

Walsmith, J. and Roubenoff, R., "Cachexia in Rheumatoid Arthritis," International Journal of Cardiology 85(1):89-99, Elsevier, Netherlands (2002).

Written Opinion for International Application No. PCT/EP2013/059460, European Patent Office, Germany, mailed Jul. 3, 2013, 4 pages.

Written Opinion for International Application No. PCT/KR2013/004145, Korean Intellectual Property Office, Republic of Korea, mailed Aug. 14, 2013, 13 pages.

(56) References Cited

OTHER PUBLICATIONS

Written Opinion for International Application No. PCT/KR2013/004176, Korean Intellectual Property Office, Republic of Korea, mailed Aug. 6, 2013, 13 pages.
Written Opinion for International Application No. PCT/KR2013/006218, Korean Intellectual Property Office, Republic of Korea, mailed Sep. 26, 2013, 26 pages.
Written Opinion for International Application No. PCT/KR2013/008438, Korean Intellectual Property Office, Republic of Korea, mailed Dec. 23, 2013, 9 pages.
Written Opinion for International Application No. PCT/KR2013/008445, Korean Intellectual Property Office, Republic of Korea, mailed Dec. 23, 2013, 12 pages.
Written Opinion for International Application No. PCT/KR2014/005031, Korean Intellectual Property Office, Republic of Korea, mailed Sep. 22, 2014, 7 pages.
Written Opinion for International Application No. PCT/KR2014/005508, Korean Intellectual Property Office, Republic of Korea, mailed Oct. 14, 2014, 13 pages.
Written Opinion for International Application No. PCT/KR2013/008459, Korean Intellectual Property Office, Republic of Korea, mailed Dec. 23, 2013, 9 pages.
Written Opinion for International Patent Application No. PCT/KR2013/004156, Korean Intellectual Property Office, Republic of Korea, mailed Aug. 14, 2013, 13 pages.
Written Opinion for International Application No. PCT/KR2014/003425, Korean Intellectual Property Office, Republic of Korea, mailed Jul. 21, 2014, 13 pages.
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).

\* cited by examiner

COMPOSITION FOR TREATING AND PREVENTING BENIGN PROSTATIC HYPERPLASIA

CROSS REFERENCE TO RELATED APPLICATIONS

This application is a continuation application of Int'l Appl. No. PCT/KR2014/010035, filed Oct. 23, 2014, which claims the benefit of KR application number 10-2013-0126666, filed on Oct. 23, 2013, all of which are herein incorporated by reference.

REFERENCE TO SEQUENCE LISTING SUBMITTED ELECTRONICALLY VIA EFS-WEB

The content of the electronically submitted sequence listing (Name: 2473_0890001_SeqListing_ST25.txt; 10,370 bytes; and Date of Creation: Apr. 15, 2016) was originally submitted in the International Application No. PCT/KR2014/010035 and is incorporated herein by reference in its entirety.

BACKGROUND OF THE INVENTION

Field of the Invention

The present invention relates to a composition for the treatment and prevention of benign prostatic hyperplasia. More particularly, the present invention relates to the composition comprising a peptide derived from telomerase and the composition is for the treatment and prevention of benign prostatic hyperplasia.

Background

Benign prostatic hyperplasia (BPH) is the most common age-related disease of male which is accompanied by lower urinary tract symptom. Related symptoms began to appear from the age of 40, but the most clinical symptoms appear from the late age of 50. BPH can cause sexual dysfunction by reduced quality of life, and the treatment and surgery for BPH can affect sexual function.

The hyperplasia causing BPH is dependent on male hormones. Especially the male hormones are necessary for normal cell proliferation in prostate as well as for inhibition of normal apoptosis. The most known endogenous cause is aging. Prostate gets bigger by aging and normal testis function. As the male hormone that prostate is depend on, testosterone plays an important role in growing and differentiating prostate and is metabolized by 5-alpha-reducatse to make dihydrotestosterone (DHT) which plays an important role in growing prostate and expressing the genes of prostate.

As exogenous causes of growing prostate, there are male hormones, estrogen, glucocorticoid and materials related to internal secretion, enzymes which are induced by diet and circumstances. The physiological effects of these exogenous causes appears via many kinds of growth factor peptides.

BPH occurs in early 20s to late 40s caused by histological changes when the male hormones and estrogen work synergistically to induce BPH. With increasing age, the rate of estrogen/DHT and then BPH increase.

Also, it was commonly known that the prostate grows up until early 20s and then it keeps its size until 50, and it depends on the very complicated interaction such as endogenous growth factors, signal pathway, regulation of cell cycles, cell division and apoptosis that the prostate maintains its balance. If transform occurs to cell cycle regulation factors, BPH may be induced.

The genetic factor can be a major factor which affect BPH. It was reported that patients having a family history of BPH has shown increase of BPH by more than 60%, and it also reported that treatment by 5α-reductase inhibitor is less effective in a group of patients having a family history of BPH. This is because, in such cases, BPH depends on non-androgen dependent pathway.

For treating BPH, surgery and medical treatment can be used. For medical treatment, administration of drugs is adjusted depending on the age and clinical progress of a patient. Recently the number of BPH patients have significantly increased in Korea and worldwide and the disease rate in young patient has also increased. Various drugs are used for treatment but their uses are limited for side-effects.

Sulpiride is type 2 dopamine receptor antagonist, which is commonly used as a depression treatment drug. Dopamine, as an intermediate product made in synthesizing pathway of adrenalin and noradrenalin, is an inhibitory neurotransmitter. Sulpiride inhibits binding of dopamine and its receptor which inhibit prolactin secretion on as dopaminergic effect and elevates the concentration of prolactin in blood. Increased prolactin by continuous administration of sulpiride induces hyperprolactinemia.

It is reported that prolactin is related to proliferation of prostate, prostate cancer and development and regulation of BPH. Also it is known that prolactin in conjunction with androgen elevates proliferation of prostate. As another mechanism, it is also known that prolactin acts as a stress hormone to elevate expression of 5α-reductase and induces proliferation of prostate. Prolactin, which is one of non-steroidal factors, relates to proliferation of prostate and induction of BPH. With age, prolactin increases but the level of testosterone declines. It is reported that prolactin induces BPH in elderly human. For rat and human, it is reported that prolactin is involved in proliferation and differentiation of prostate.

According to this report, prolactin is considered to be induced by receptors through signal transduction pathways.

PRIOR ART DOCUMENT

Patent Document

KR 2011-0062943 A
KR 2011-0057049 A
EP 1020190 A3

Non-Patent Document

MCCONNELL, John D., et al. 'The effect of finasteride on the risk of acute urinary retention and the need for surgical treatment among men with benign prostatic hyperplasia', New England Journal of Medicine, 1998, Vol. 338, No. 9, pp. 557-563.

BRIEF SUMMARY OF THE INVENTION

Technical Problem

Thus, the present inventors have tried to develop a composition for treatment and prevent of BPH which has minimum side-effect and superior treatment effect, and have completed the present invention.

The present inventors have discovered that the peptide derived from telomerase can have excellent effects for treatment and prevent of BPH and have completed the present invention.

The object of the present invention is to provide a composition having an effect in treating and preventing BPH.

Solutions for the Problem

To solve the above-mentioned technical problem, according to the present invention, a composition for treating and preventing BPH which includes the peptide or the fragment of the peptide comprising a sequence of SEQ ID NO:1 (hereinafter, "PEP1", "GV1001", or "GV") or a sequence having homology 80% or more of SEQ ID NO:1 is provided.

In the composition for treating and preventing BPH according to the present invention, said fragment may comprise 3 or more amino acids.

In the composition for treating and preventing BPH according to the present invention, the peptide may be comprised in the concentration of 0.01 mg to 1 mg, preferably 0.56 mg (4 nmol peptide/kg body weight).

In the composition for treating and preventing BPH according to the present invention, the composition may be a pharmaceutical composition.

In the composition for treating and preventing BPH according to the present invention, the composition may be a food composition.

According to another embodiment of the present invention, the method for treating and preventing BPH by administrating the composition for treating and preventing BPH to subject in need of is provided.

In the method for treating and preventing BPH according to the present invention, the administration of the composition may be done in 3 times a week.

Effect of the Invention

The composition, according to the present invention, which comprises the peptide having the sequence of SEQ ID NO:1 or the sequence of 80% or more homology of it, has excellent effect for treating and preventing BPH with less side effects.

BRIEF DESCRIPTION OF THE DRAWINGS/FIGURES

DETAILED DESCRIPTION OF THE INVENTION

Best Mode of Examinating the Invention

Figure 1:
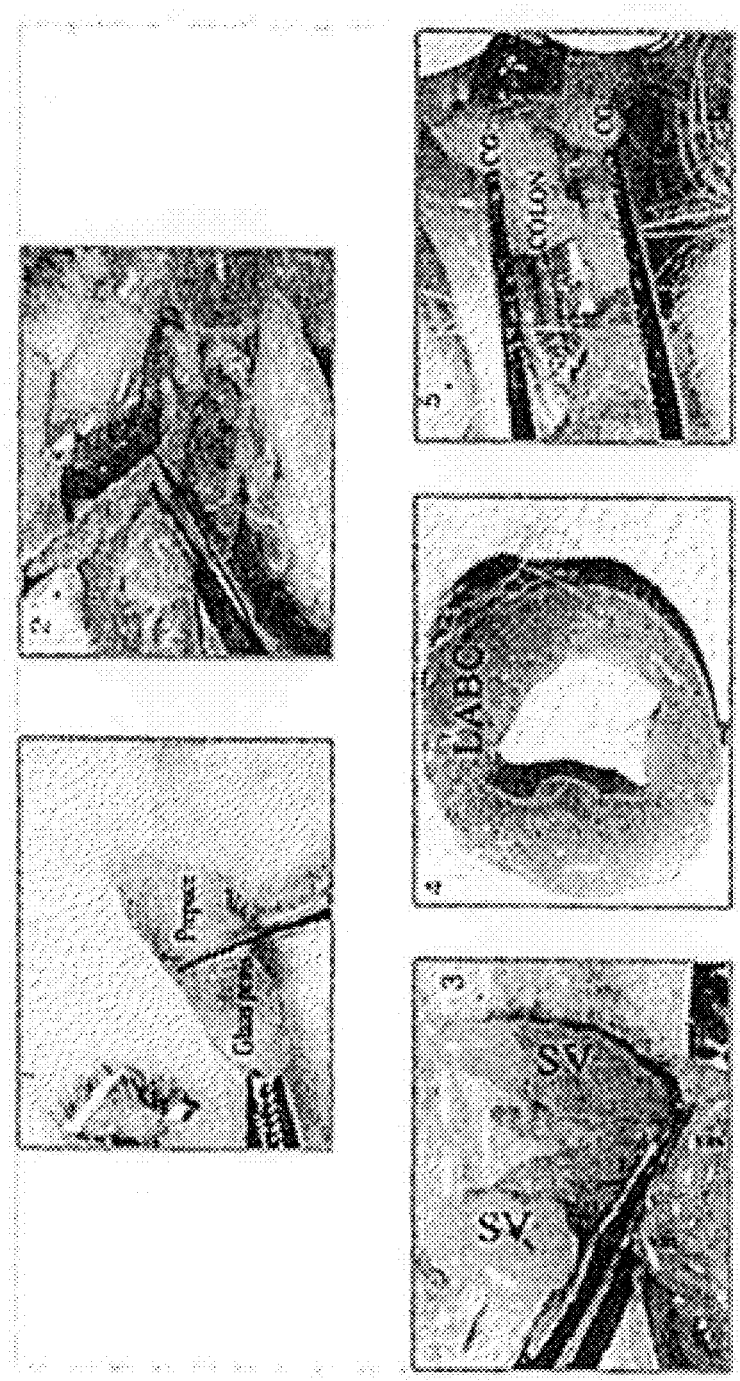
FIG. 1 represents a photograph of a process for removing the target organs to measure weight of them.

Since the present invention can be adapted to various fields of use and in various modifications, the followings are more detailed descriptions of the present invention. Nevertheless, this is no means to limit the form of practical application; it should be understood that the intention is to include the concept and the extent of technology in all of the modifications, equivalents to alternatives. In describing the present invention, if any detailed description about the prior art is considered to deteriorate the fundamental principles of the present invention, the description will be omitted.

Telomere is known as a repetitive sequence of genetic material found at the ends of chromosomes that prevent chromosomes from damage or merging onto other chromosomes. The length of the telomere is shortened at each cell division, and after a certain number of cell division, the telomere length is extremely shortened to the extent in which the cell stops dividing and dies. On the other hand, the elongation of telomeres is known to extend the life span of a cell. For example, cancer cells excrete an enzyme called telomerase, which prevents shortening of telomeres, thus resulting in proliferation of cancer cells. The inventors of the present invention have identified that a peptide derived from telomerase is effective in treating and preventing BPH and have completed the present invention.

In an embodiment of the present disclosure, a peptide of an amino acid sequence SEQ ID NO: 1, a peptide fragment of the above-mentioned peptide or a peptide having a sequence identity of 80% or greater to the amino acid sequence of the above-mentioned peptide comprise telomerase, in particular, telomerase derived from *Homo sapiens* The peptides disclosed herein may include peptides comprising an amino acid sequence at least 80%, at least 85%, at least 90%, at least 95%, at least 96%, at least 97%, at least 98%, at least 99% of sequence homology with the peptide of SEQ ID NO 1 or a fragment thereof. Moreover, the peptides disclosed in the present invention may include peptides having differences from SEQ ID NO 1 or a fragment thereof in at least one amino acids, at least 2 amino acids, at least 3 amino acids, at least 4 amino acids, at least 5 transformed amino acids, at least 6 transformed, amino acids, or at least 7 amino acids.

In one embodiment of the present invention, changes in amino acids include modifications of peptide's physical and chemical characteristics. For example, amino acid modification can be performed for improving thermal stability of the peptide, altering substrate specificity, and changing the optimal pH.

The term "amino acid" herein includes not only the 22 standard amino acids that are naturally integrated into a peptide but also the D-isomers and modified amino acids. Therefore, in a specific embodiment of the present invention, a peptide herein includes a peptide having D-amino acids. In addition, a peptide may include non-standard amino acids such as those that have been post-translationally modified. Examples of post-translational modification include phosphorylation, glycosylation, acylation (including acetylation, myristorylation, palmitoylation), alkylation, carboxylation, hydroxylation, glycation, biotinylation, ubiquitinylation, modification in chemical properties (e.g. β-removing deimidation, deamidation) and structural modification (e.g. formation of disulfide bridge). Also, changes of amino acids include the changes of amino acids that occur due to chemical reaction during the combination process with cross-linkers for formation of a peptide conjugate, such as changes in an amino group, carboxyl group or side chain.

A peptide disclosed herein may be a wild-type peptide that has been identified and isolated from natural sources. Meanwhile, when compared to SEQ ID NO: 1 or its fragments, the peptides disclosed herein may be artificial variants that comprise one or more amino acids substituted, deleted and/or inserted. Amino acid alteration in wild-type polypeptides—not only in artificial variants—comprises protein folding and/or conservative substitutions of amino acids that do not influence activities significantly. Examples of conservative substitutions may be within the groups of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activities are known in the art. Most common occurring alterations are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations thereof. Other examples of conservative substitutions are shown in the following Table 1:

| Original amino acid | Examples of residue substitution | Preferable residue substitution |
|---|---|---|
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | Ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | Ala | Ala |
| Ser (S) | thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala; norleucine | Leu |

The substantial transformation of the biological properties of peptides are performed by selecting a significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in the target area, or (c) the efficacy of maintaining the bulk of the side chain. Natural residues are divided into groups by general side chain properties as the following:

(1) hydrophobicity: Norleucine, met, ala, val, leu, ile;
(2) neutral hydrophilicity: cys, ser, thr;
(3) acidity: asp, glu;
(4) basicity: asn, gln, his, lys, arg;
(5) residue that affects chain orientation: gly, pro; and
(6) aromaticity: trp, tyr, phe.

Non-conservative substitutions may be performed by exchanging a member of the above classes to that of a different class. Any cysteine residues that are not related in maintaining the proper three-dimensional structure of the peptide can typically be substituted into serine, thus increasing the oxidative stability of the molecule and preventing improper cross-linkage. Conversely, improvement of stability can be achieved by adding cysteine bond(s) to the peptide.

Another type of amino acid variants of peptides are those having a changed pattern of peptide glycosylation. The term "change" herein means deletion of at least one carbohydrate residues that are found in a peptide and/or addition of at least one glycosylated residues that do not exist within a peptide.

Glycosylation in peptides are typically N-linked or O-linked. The term "N-linked" herein refers to that carbohydrate residues are attached to the side chain of asparagine residues. As tripeptide sequences, asparagine-X-serine and asparagine-X-threonine (wherein the X is any amino acid except proline) are a recognition sequence for attaching a carbohydrate residue enzymatically to the side chain of asparagine. Therefore, with the presence of one of these tripeptide sequences in a polypeptide, the potential glycosylation sites are created. "O-linked glycosylation" means attaching one of sugar N-acetylgalactosamine, galactose, or xylose to hydroxyl amino acids. The hydroxyl amino acids are most typically serine or threonine, but 5-hydroxyproline or 5-hydroxylysine can be used.

Addition of a glycosylation site to a peptide is conveniently performed by changing an amino acid sequence to contain a tripeptide sequence mentioned above (for N-linked glycosylation sites). These changes may be made by addition of at least one from serine or threonine residues to the first antibody sequence, or by substitution with these residues (for O-linked glycosylation sites).

Also the peptide according to the present invention comprising the amino acid sequence of SEQ ID NO 1, the peptide comprising the amino acid sequence having more than 80% homology with above-mentioned sequence, or fragments of the above-mentioned peptide has the advantage of low toxicity and high stability in living matter. The SEQ ID NO 1 as used herein is a telomerase-derived peptide comprised of 16 amino acids.

SEQ ID NO: 1 EARPALLTSRLRFIPK

An embodiment of the present invention provides the composition for treating and preventing BPH which comprises the peptide comprising the amino acid sequence of SEQ ID NO 1, the peptide comprising the amino acid sequence having more than 80% homology with above-mentioned sequence, or fragments of the above-mentioned peptide.

In one embodiment of the present invention, the composition may have applications with all animals including human, dog, chicken, pig, cow, sheep, guinea pig, and monkey.

In one embodiment of the present invention provides the pharmaceutical composition, for treating and preventing BPH which comprises the peptide comprising the amino acid sequence of SEQ ID NO: 1; the peptide comprising the amino acid sequence having more than 80% homology with above-mentioned sequence, or fragments of the above-mentioned peptide. In the pharmaceutical composition according to one embodiment of the present invention may be administered through oral, rectal, transdermal, intravenous, intramuscular, intraperitoneal, in the bone marrow, epidural or subcutaneous routes.

Forms of oral administration may be, but not limited to, tablets, pills, soft or hard capsules, granules, powders, solution, or emulsion. Forms of non-oral administration can be, but not limited to, injections, drips, lotions, ointments, gels, creams, suspensions, emulsions, suppository, patch, or spray.

In one embodiment of the present invention, the pharmaceutical composition, if necessary, may contain additives, such as diluents, excipients, lubricants, binders, disintegrants, buffers, dispersants, surfactants, coloring agents, aromatics or sweeteners. In one embodiment of the present invention, the pharmaceutical composition may be manufactured by conventional methods of the industry in the art.

In one embodiment of the present invention, the dose of the active ingredient of the medical composition may vary according to the patient's age, sex, weight, pathology and state, administration route, or prescriber's judgment. Dosage based on these factors may be determined within levels of those skilled in the art, and the daily dose, for example, may be, but not limited to, 0.01 µg/kg/day to 10 g/kg/day, specifically 0.1 µg/kg/day to 1 mg/kg/day, more specifically the 1 µg/kg/day to 0.1 g/kg/day, more specifically the 1 µg/kg/day to 10 mg/kg/day, preferably 1 µg/kg/day to 1 mg/kg/day, preferably 0.005 mg/kg/day to 0.05 mg/kg/day, most preferably 0.01 mg/kg/day, but it can be adjusted if there is the differences of the effect according to administration dosage. For an adult, it is preferable that the dosage for the administration is 0.1 mg to 1 mg, preferably 0.4 mg to 0.6 mg, especially the dosage of 0.56 mg is most preferred.

In one embodiment of the present invention, the pharmaceutical composition may be administered, but not limited to, 1 to 3 times a day.

In one embodiment of the present invention, the composition may contain 0.01 g/L to 1 kg/L, specifically 0.1 g/L to 100 g/L, more specifically 1 g/L to 10 g/L of a peptide comprising amino acid sequence of at least one of SEQ ID NO 1, a peptide comprising an amino acid sequence at least 80% sequence homology with the above-mentioned sequences, or a fragment of the above-mentioned thereof. When the peptide is contained in the above-mentioned ranges, both of safety and stability of the composition can be satisfied and the ranges are appropriate in terms of cost-effectiveness.

In one embodiment of the present invention provides the food composition for treating and preventing BPH which comprises the peptide comprising the amino acid sequence of SEQ ID NO 1, the peptide comprising the amino acid sequence having more than 80% homology with above-mentioned sequence, or fragments of the above-mentioned peptide.

In one embodiment of the present invention, food composition is not limited to specific forms, but, for example, may be tablets, granules, powder, liquid, and solid forms. Each form may be formed with ingredients commonly used in the industry appropriately chosen by those skilled in the art, in addition to the active ingredient, and may produce a synergic effect in combination of other ingredients.

The terms used herein is intended to be used to describe the embodiments, not to limit the present invention. Terms without numbers in front are not to limit the quantity but to show that there may be more than one thing of the term used. The terms "comprising", "having", "including" and "containing" shall be interpreted openly (i.e. "including but not limited to").

The reason why the numeric values are mentioned as the ranges is only because it is convenient to describe in the range rather than individual numbers. Unless otherwise noted, each individual numeric values should be understood to be described individually and integrated into the specification. Thresholds in all ranges are included and can be combined independently.

Unless otherwise noted or clearly contradicting in context, all methods mentioned herein can be performed in a proper order. The use of any one embodiment and all embodiment, or exemplary language (e.g., "such as", "like ~"), unless included in the claims, is used to more clearly describe the present invention, not to limit the scope of the present invention. Any language herein outside of the claims should not be interpreted as a necessity of the present invention. Unless defined otherwise, technical and scientific terms used herein have meanings ordinarily understood by a person skilled in the art that the present invention belongs to.

The preferred embodiments of the present invention include the best mode known to the inventors to perform the present invention. Variations in the preferred embodiments can become clear to those skilled in the art after reading the statements above. The present inventors' hope that those skilled in the art can use the variations adequately and present invention be conducted in other ways than listed herein. Thus, the present invention, as allowed by the patent law, includes equivalents, modifications and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

Embodiments for Establishing the Present Invention

Hereinafter, the present disclosure will be described in detail through examples and test examples. However, the following examples and test examples are for illustrative purposes only and it will be apparent to those of ordinary skill in the art that the scope of the present disclosure is not limited by the examples and test examples.

EXAMPLE 1

Synthesis of a Peptide

The peptide of SEQ ID NO: 1 was synthesized according to the conventionally known method of solid phase peptide synthesis. More specifically, the peptide was synthesized by coupling each amino acid from C-terminus through Fmoc solid phase peptide synthesis, SPPS, using ASP48S (Peptron, Inc., Daejeon ROK). Those peptides with their first amino acid at the C-terminus being attached to a resin were used as follows NH2-Lys(Boc)-2-chloro-Trityl Resin
NH2-Ala-2-chloro-Trityl Resin
NH2-Arg(Pbf)-2-chloro-Trityl Resin All the amino acids to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in an acid. Examples include the followings:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

HBTU[2-(1H-Benzotriazole-1-yl)-1,1,3,3-tetamethylaminium hexafluorophosphate]/HOBt [N-Hydroxybenzotriazole]/NMM [4-Methylmorpholine] were used as the coupling reagents. Piperidine in 20% DMF was used to remove Fmoc. In order to remove the protection, from residues or to separate the synthesized peptides from Resin, cleavage cocktail [TFA (trifluoroacetic acid)/TIS (triisopropylsilane)/EDT (ethanedithiol)/H2O=92.5/2.5/2.5/2.5] was used.

The peptide synthesis was performed by using solid phase scaffold with the repetition of the following processes: starting with the amino acid protection, separate reaction of each amino acid, washing with solvents, and deprotection. Each peptide was synthesized by using the solid phase scaffold combined to starting amino acid with the amino acid protection, reacting the corresponding amino acids separately, washing with a solvent and deprotected, and repeating the processes. Upon the release from the resin, the synthesized peptides were purified by HPLC, validated by Mass Spectrometry, and freeze-dried, and verify for synthesis by MS, and then freeze-dried.

The purity of the prepared peptide was found to be 95% or higher by high-performance liquid chromatography.

Specific synthesis process of PEP 1 may be as follows:
1) Coupling

The amino acid (8 equivalent) protected with NH2-Lys(Boc)-2-chloro-Trityl Resin, and coupling agent HBTU (8 equivalent)/HOBt (8 equivalent)/NMM (16 equivalent) melted in DMF were mixed together, and incubated at room temperature (RT) for 2 hr. Following the incubation, the reaction mixture was subjected to the sequential washes of DMF, MeOH, and DMF.

2) Fmoc Deprotection

Piperidine in 20% DMF was added and incubated at RT for 5 minutes 2 times, then sequentially washed with DMF, MeOH, and DMF.

3) Making the basic framework of peptide, NH2-E(OtBu)-A-R(Pbf)-P-A-L-L-T(tBu)-S(tBu)-R(Pbf)L-R(Pbf)-F-I-P-K(Boc)-2-chloro-Trityl Resin) by repeating the above mentioned-reactions 1) and 2).

4) Cleavage: Cleavage. Cocktail was added to the completely synthesized peptide, thus separating the synthesized peptide from the resin.

5) Pre-chilled diethyl ether was added into the obtained mixture, and then centrifugation was used to precipitate gathered peptide.

6) After purification by Prep-HPLC, the molecular weight was confirmed by LC/MS and lyophilized to produce in a powder form.

EXAMPLE 2

Verifying the Effect of PEP1 to BPH by the Experiment Using BPH Induced Animal Model 1) Preparation of BPH Induced Animal Model As androgen, the most commonly used hormone in the body is testosterone. But the most powerful hormone of androgens related to development of prostate is 5α-dihydrotestosterone (DHT) which is made by combining testosterone and 5α-reductase. In rat, when sulpiride is administrated for 30 days in the concentration of 40 mg/kg, it inhibits type 2 dopamine receptor to increase the concentration of prolactin in the body and induce hyperprolactinemia to activate 5α-reductase and it shows the synergic effect by reacting with testosterone. It is reported that DHT made by hyperprolactinemia make more gaining weight in lateral lobe than dorsal lobe or ventral lobe of prostate. Based on this fact, the experiment using PEP1 according to example 1 only or co-administration with other test material to BPH induced animal model was done as follows. Mature Sprague-Dawley male rats (6 weeks old) was purchased from Jae-il Experimental Animal Center and raised a week (7 weeks old, 49 days) for purification, and then it was used for the experiment. For inducing BPH, sulpiride (40 mg/kg) was administrated orally per once a day for 30 days. Every experiment followed the result of the prior experiment (Van Coppenolle et al., 2001). Administrating the test materials started in every 10 a.m. for every animal. After administrating the test materials, the general status and special symptoms of every animal were observed every day. Also before administrating the test materials, the body weights of every animal were measured and recorded.

2) Test Materials and Dosage of Administration

Sulpiride as test material was purchased from Sigma Chemical Co. (St. Louis, Mo., USA) and used for the experiment. The inventors make sulpiride (40 mg/kg) be administrated once a day for 60 days by intraperitoneal injection sequentially to induce BPH by hyperprolactinemia. Sulpiride was solved in the 0.1 N HCl solution first and then neutralized to pH 7.0 by using the 0.1 N NaOH solution every time before administrating of the test materials. For the group of co-administration, PEP1 according to the example 1 and finasteride was administrated after administration of sulpiride by intraperitoneal injection. PEP1 0.01, 0.1, 1 and 10 mg/kg) is freshly made before using and administrated by subcutaneous injection. Finasteride was made by using 15% Ethanol/Corn oil (v/v) as vehicle every day. The dosage of the administration was calculated based on the concentration of 0.5 ml/kg with reflecting the body weight measured every day. The administration was done to 7 groups each as following Table 2 to verifying the effect of PEP1 to BPH.

TABLE 2

| group | usage | path | dosage |
|---|---|---|---|
| 1 | Vehicle only | s.c | 0.5 ml/kg/day |
| 2 | sulpiride: 40 mg/kg/day | i.p | 0.5 ml/kg/day |
| 3 | PEP1 (0.01 mg/kg, s.c.) + sulpiride (40 mg/kg/day, i.p.) | s.c | 0.5 ml/kg/day |
| 4 | PEP1 (0.1 mg/kg, s.c.) + sulpiride (40 mg/kg/day, i.p.) | s.c | 0.5 ml/kg/day |
| 5 | PEP1 (1 mg/kg, s.c.) + sulpiride (40 mg/kg/day, i.p.) | s.c | 0.5 ml/kg/day |
| 6 | PEP1 (10 mg/kg, s.c.) + sulpiride (40 mg/kg/day, i.p.) | s.c | 0.5 ml/kg/day |
| 7 | finasteride(10 mg/kg, oral) + sulpiride (40 mg/kg/day, i.p.) | s.c | ml/kg/day |

(i.p = intraperitoneal, s.c = subcutaneous)

1) For BPH Induced Model, after the Experiment of Administrating PEP1 and the Test Materials, Collecting Organs of Animals Preserving them and Measuring Weights of them In 24 hours after administrating the test materials in 60 days all animals were anesthetized by ether and then their blood collected from abdominal aorta was separated into the serum. The separated serum was preserved at −80° C. to analyze hormone.

For all animals, after testing the exist of prepuce separation (PPS), the accessory reproductive glands such as gland penis (Gp), seminal vesicles and coagulating glands (SV), ventral prostate (VP), cowpers's gland (CpG), levator aniplus bulbocavernosus muscle (LABC) ware separated sequentially from the body. The detailed separation process followed OECD protocol.

For the separation of Gp, as mentioned in FIG. 1, grip Gp section by using tweezer and cut separation line of prepuce. For a lung, as mentioned in FIG. 1, after separating bladder from abdominal muscle layer, expose the left and right lobes of the lung covered by lipid layer, reveal the bladder to SV, separate the lipid from the left and right lobes of the lung by using tweezer, cut the left lobe of the lung from urethra after pulling by using micro tweezer, and cut the right lobe of the lung after exposing from urethra by using forceps. For the SV comprising coagulating gland, as mentioned in FIG. 1, prepare paper towels beneath SV to classify muscle, lipid layer and glands. Fix the base of SV comprising seminiferous tubes connected with urethra by using clamp to prevent leakage during the removal of seminal vesicles. After removing the lipid, clean up related accessory organs, remove the clamp and put the seminal vesicles on the dish to measure its weight.

Figure 2:
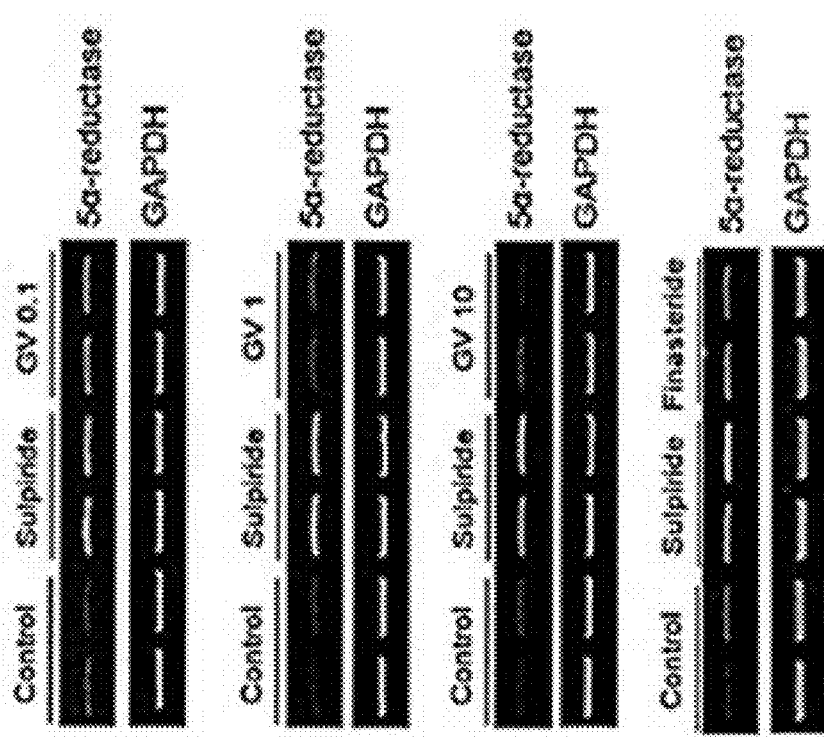
FIG. 2 represents a photograph of an electrophoresis, in the experiment to verifying the effect of PEP1 to the treatment of BPH, which shows the result of the effect to 5α-reductase expression in the ventral prostate of each experimental group by using RT-PCR.

2) The Effect of the Administration of PEP1 to the Expression of 5α-Reductase in BPH Induced Animal Test Model After administrating sulpiride with test materials for 60 days and collecting ventral prostate, the effect to the expression of 5α-reductase was measured by using RT-PCR. Specifically, total RNA separated from ventral prostate (25 mg) and re-suspended by adding DEPC-treated water. The then RNA was quantified by using spectrophotometer. The first strand cDNA was synthesized by methods of Torres and Ortega (2004). The profile of PCR had denaturing 94° C. (30 sec), annealing 55° C. (30 sec), extension 72° C. (30 sec) and 30-35 cycle times. For the control of quantification in electrophoresis, GAPDH whose expression level is not changed by other drugs was used. As a result, the increased level of 5α-reductase by administration of sulpiride was inhibited in the group of PEP1 administration in dose-dependent and the inhibitory effect in high-dose PEP1 administration group (GV 10, the group of administrating PEP1 in 10 mg) was higher than the group of finasteride administration (see FIG. 2). Thus PEP1 can give the dose-dependent treatment and improvement effect to BPH by inhibiting 5a-reductase.

3) The Effect of PEP1 Administration to the Organs of BPH Induced Test Animal Model In below Table 3, it is reported that peptide PEP1 effected to the weight of seminal vesicle, the weight of prostate and prostate index in each group of experiment. The prostate index described in Table 3 was calculated by using the equation of "body weight/Final prostate weight".

TABLE 3

| Group | Usage | Weight of seminal vesicle (g) | Weight of prostate (g) | Prostate index |
|---|---|---|---|---|
| 1 | Control | 0.84 ± 0.06 | 0.65 ± 0.05 | 0.206 |
| 2 | Sulpiride 40 mg/kg 60 days | 1.23 ± 0.11 | 1.59 ± 0.05 | 0.303 |
| 3 | Sulpiride 40 mg/kg 60 days + PEP1 0.01 mg/kg | 0.97 ± 0.07 | 1.13 ± 0.07 | 0.208 |
| 4 | Sulpiride 40 mg/kg 60 days + PEP1 0.1 mg/kg | 1.03 ± 0.12 | 1.32 ± 0.05 | 0.265 |
| 5 | Sulpiride 40 mg/kg 60 days + PEP1 1 mg/kg | 0.81 ± 0.04 | 0.94 ± 0.08 | 0.198 |
| 6 | Sulpiride 40 mg/kg 60 days + PEP1 10 mg/kg | 0.41 ± 0.03 | 0.57 ± 0.05 | 0.132 |
| 7 | Sulpiride 40 mg/kg 60 days + Finasteride 5 mg/kg | 0.49 ± 0.02 | 0.75 ± 0.06 | 0.157 |

Figure 3:
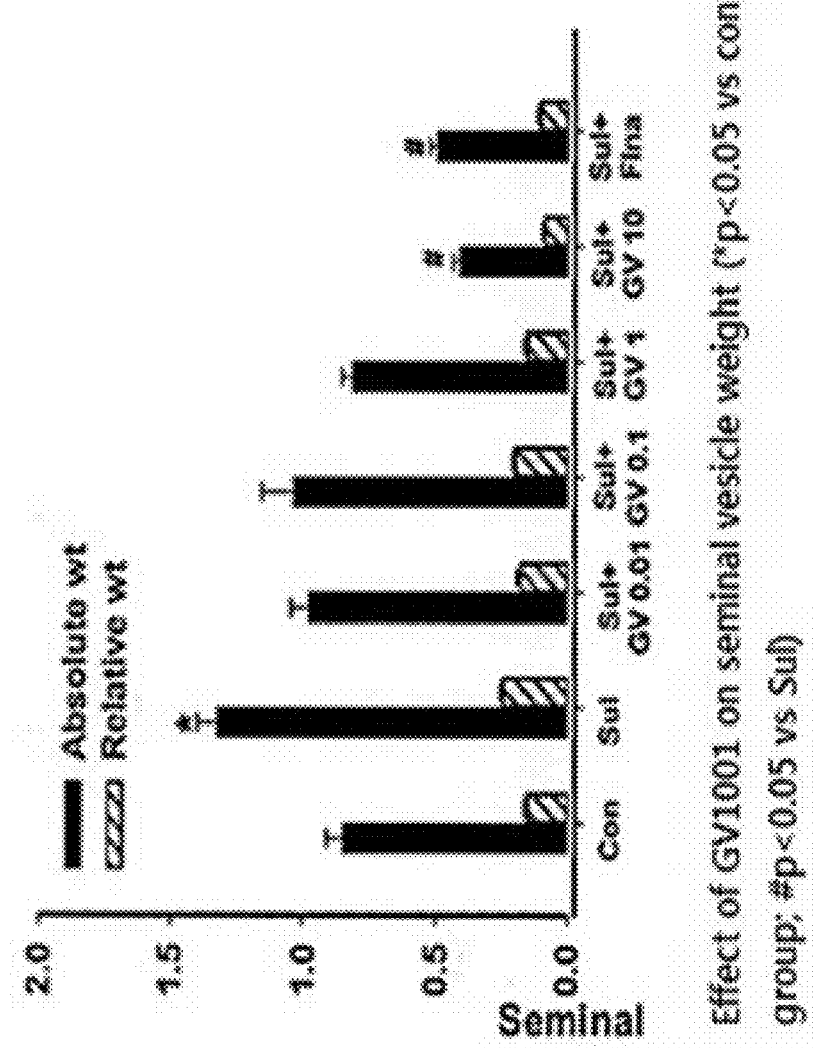
FIG. 3 represents a graph, in the experiment to verifying the effect of PEP1 to the treatment of BPH, which shows the result of the measured weight of seminal vesicle in each experimental group.
Figure 4:
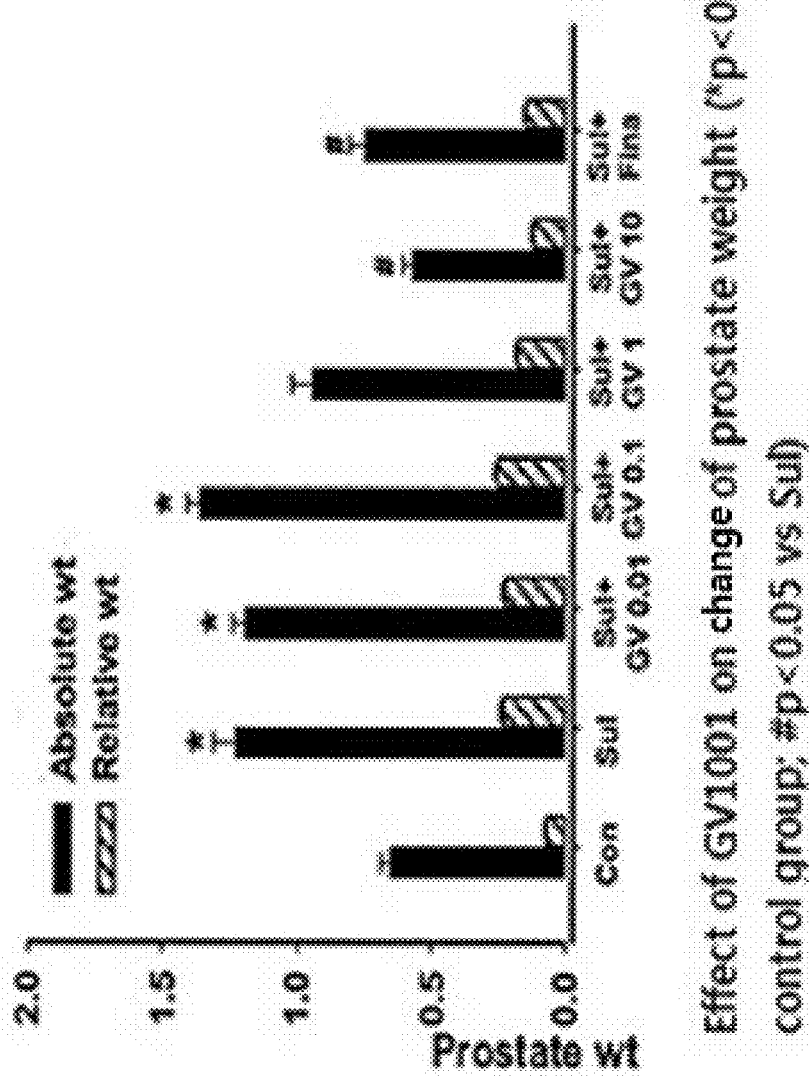
FIG. 4 represents a graph, in the experiment to verifying the effect of PEP1 to the treatment of BPH, which shows the result of the measured weight of prostate in each experimental group.

The result which was described in Table 3 was turn into a graph, i.e. observing the result of measuring the seminal vesicles after administrating PEP1 and finasteride (5 mg/kg) in BPH induced animal followed by administrating sulpiride, and the graph shows that the weight of seminal vesicle in the case of high-dose PEP1 administration (10 mg/kg) was significantly decreased (see FIG. 3). Also, the case of co-administration of sulpiride and PEP1 shows that the weight of prostate was significantly decreased in BPH induced animal model (see FIG. 4). If P-value is under 0.05, it means a significant result.

Therefore, through the result of example 2, the administration of PEP1 to BPH induced animal model by sulpiride can be effective to, dose-dependently, the decrease of expression of 5α-reductase, the decrease of the weight of seminal vesicles and the decrease of the weight of prostate. Thus, the administration of PEP1 can be effective to treat and improve BPH related disease symptoms which comes from the expression of 5α-reductase and the weight of reproductive organs.

EXAMPLE 3

Verifying the Effect of PEP1 to BPH by Observation of Changes in the Proliferation of Prostate Stromal Cell and Epithelial Cell by DHT 1) Preparation for Test Cells and Process of the Experiment Testosterone changes into DHT by 5α-reductase when it is injected to the body and it induces proliferation of prostate cells to cause BPH. Based on this, the experiment has been done to observe the effect on proliferation of prostate cell line by using administration of PEP1 according to example 1. As the cell lines, the WPMY-1 (prostate stromal cell line) and the RWPE-1 (prostate epithelium cell line) from animal models are used. For the experiment, WPMY-1 ($2.5 \times 10^3$ cells) and RWPE-1 ($1 \times 10^4$ cells) were seeded to 96 well which has separated experimental groups like Table 4 to observe the proliferation change. The proliferation change was observed by putting CCK-8 solution into each well of the media per 10 μL after suctioning the culture media, and measuring optical density for 1-4 hour at 450 nm wavelength.

2) Confirmation of the Observed Result and the Effects

Figure 5:
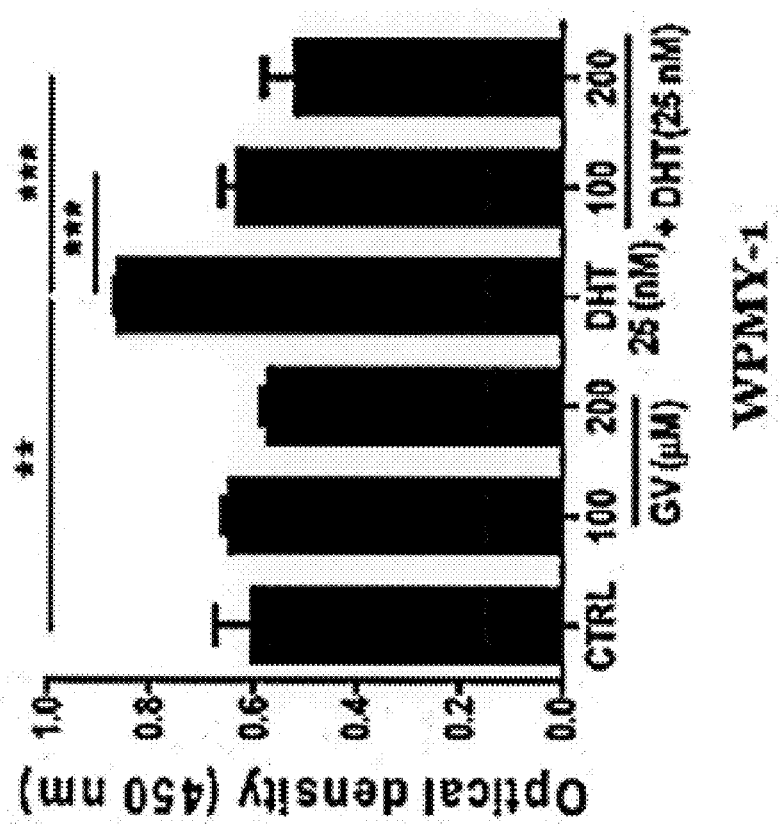
FIG. 5 represents a graph which shows the amount of cell proliferation in the stromal cell line of the BPH induced animal model (WPMY-1) which was treated by PEP1.
Figure 6:
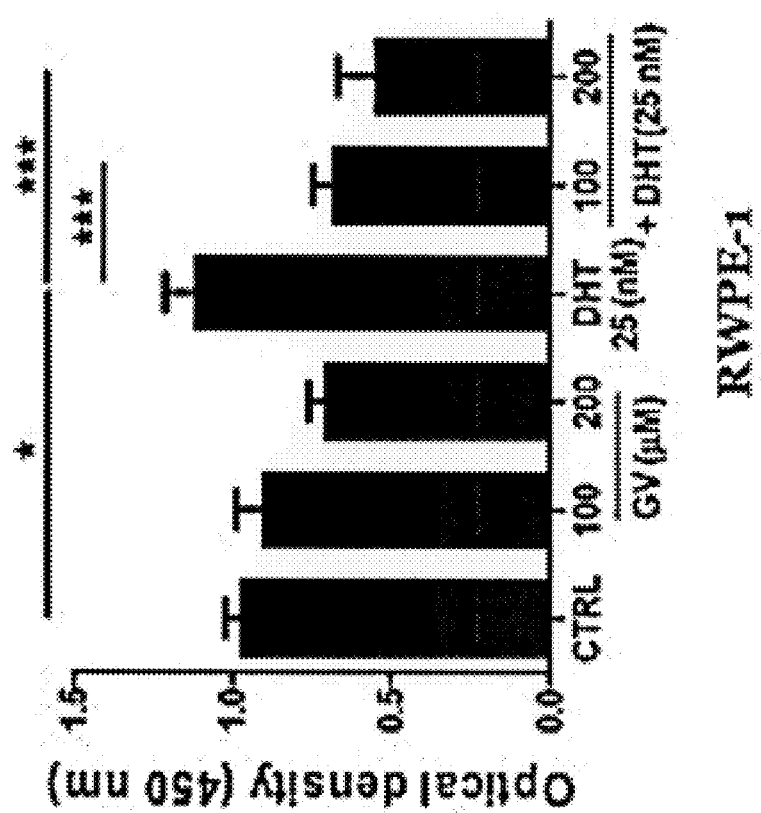
FIG. 6 represents a graph which shows the amount of cell proliferation in the epithelial cell line of the BPH induced animal model (RWPE-1) which was treated by PEP1.

In DHT non-treated groups (1-3 groups), there was not significant differences between the group of not administrating PEP1 (1 group) and the groups of administrating PEP1 (2 and 3 groups) in both WPMY-1 and RWPE-1. In DHT treated groups (4-6 groups) there is significant differences between the group of not administrating PEP1 (4 group) and the groups of administrating PEP1 (5 and 6 groups), and the groups which were treated by PEP1 shows significant inhibition effect to proliferation (see Table 4 and FIG. 5, 6). Therefore, PEP1 can be effective in the inhibition of proliferation of prostate cells, which affects DHT-induced BPH.

TABLE 4

Treatment condition for each cell line group

| group (WPMY-1 and RWPE-1 in common) | Treatment |
|---|---|
| 1 (CTRL) | Cell line only |
| 2 (100) | Treating PEP1 100 μM to cell line |
| 3 (200) | Treating PEP1 200 μM to cell line |
| 4 (DHT25) | Treating DHT 25 μM to cell line at the same time |
| 5 (100) | treating PEP1 (100 μM) and DHT (25 μM) to cell line at the same time |
| 6 (200) | treating PEP1 (200 μM) and DHT (25 μM) to cell line at the same time |

EXAMPLE 4

Verifying the Binding Ability to Androgen Receptor and the Mechanism of Inhibiting BPH of PEP1

1) Preparation for Test Cells and Process of the Experiment

DHT created by 5α-reductase promotes proliferation of prostate cell by binding to androgen receptor and causes BPH. Based on this, the experiment related to proliferation of prostate cell which administrates PEP1 according to example 1 to the body has been done. As the cell lines, WPMY-1 and RWPE-1 from animal models were used. WPMY-1 and RWPE-1 were separated into the group of anti-androgen receptor and the group of isotype control, incubated with each anti-bodies to do competitive test by putting PEP1-FITC (fluorescein isothiocyanate) in it, and measured by value of fluorescence for the result. The fluorescence value was measured by using flow-cytometry method.

2) Confirmation of the Observed Result and the Effects

Figure 7:
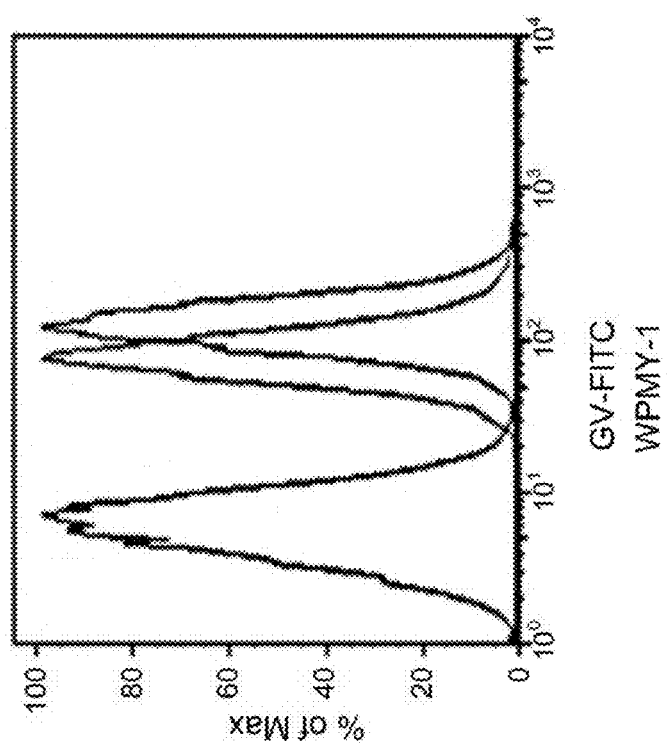
FIG. 7 represents a graph which shows the binding ability of PEP1 to androgen receptor measured by using the conjugate of PEP1-FITC (Fluorescein isothiocyanate) in the stromal cell line of the BPH induced animal model (WPMY-1).
Figure 8:
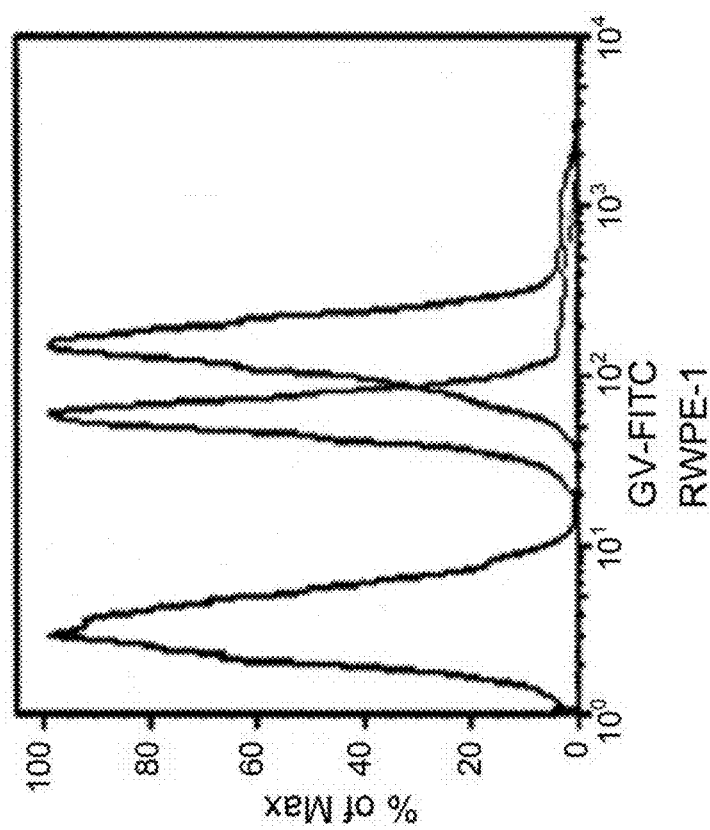
FIG. 8 represents a graph which shows the binding ability of PEP1 to androgen receptor measured by using the conjugate of PEP1-FITC (Fluorescein isothiocyanate) in the epithelial cell line of the BPH induced animal model (RWPE-1).

For each of WPMY-1 and RWPE-1, the fluorescence values were measured in which a case reacted to the anti-androgen receptor isotype control antibody first (competed with antibody, peak of the farthest to the right), other case reacted to the anti-androgen receptor antibody (competed with antibody, peak of the middle), and another case not reacted to two antibodies neither bound to FITC (peak of the farthest to the left) (see FIG. 7 and FIG. 8). In case of competing with anti-androgen receptor isotype control antibody, PEP1 bound to anti-androgen receptor so the value of fluorescence of PEP1-FITC conjugate was increased (the peak shifted to the right of histogram in the graph). In case of competing with anti-androgen receptor, PEP1 bound weakly to anti-androgen receptor so the value of fluorescence was decreased (the peak shifted to the left of histogram in the graph). Therefore, for considering that PEP1 inhibits BPH induced by DHT which binds to anti-androgen receptor, PEP1 can affect BPH by binding to an anti-androgen receptor directly.

EXAMPLE 5

Verifying In Vivo Effectiveness of PEP1 to BPH by Using BPH Induced Animal Model 1) Preparation of Test Animal The experiment used 6-8 weeks old male C57BL/6 (n=10/group) mice and the mice were raised in the SPF (specific pathogen free) area of experimental animal laboratory in Medical College of Seoul University. Testosterone enanthate (TE, purchased from EVER Pharma Hena GmbH, Germany) for injection 50 mg and estradiol valerate (purchased from EVER Pharma Hena GmbH, Germany) 0.5 mg are respectively mixed into 70 μl volume of micro-osmotic pump (Alzet pump, purchased from DURECT Corporation, USA), and the pump was transplanted in the back of mouse under anesthetic. The pump was designed to release the hormone in the concentration of 0.11 μl per an hour in 28 days (2 weeks) into the mouse by using osmosis phenomenon.

2) Test Materials and Administration Dosage

As test materials, testosterone and finasteride were used. For prepared animal models, per one subject (25 g mouse model) 250 μg of PEP1 according to example 1 and 2500 μg of finasteride (in DMSO or cyclodextrin, purchased from Sigma Aldrich, USA) were administered subcutaneously (injection) respectively every day. After 2 weeks from injecting test materials (4 weeks after transplanting the pump to animal model), the blood was collected from supraorbital vein and centrifuged in 14000 rpm, 4° C., 30 min to separate blood serum, and the prostate was extracted and froze in liquid nitrogen at −70° C. or fixed in a fixing fluid. The test groups for experiment are described in Table 5 below.

TABLE 5

| Test group | Experiment |
|---|---|
| CTL (control) | Normal mouse (treated by neither testosterone nor estradiol) |
| H-CTL (BPH) | BPH induced mouse model (treated with testosterone and estradiol) |
| H-GV (PEP1) | Administration of PEP1 to BPH induced mouse model |
| H-F (Finasteride) | Administration of finasteride to BPH induced mouse model |

3) Measuring the Decrease of the Factors which Induce BPH

Figure 9:
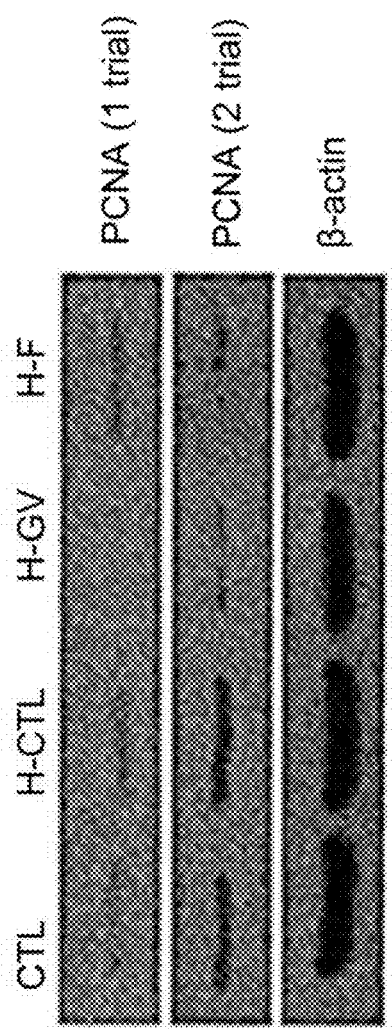
FIG. 9 represents a photograph of an electrophoresis which shows the effect of PEP1 to the expression of PCNA (proliferating cell nuclear antigen), which is increased in BPH induced model.
Figure 10:
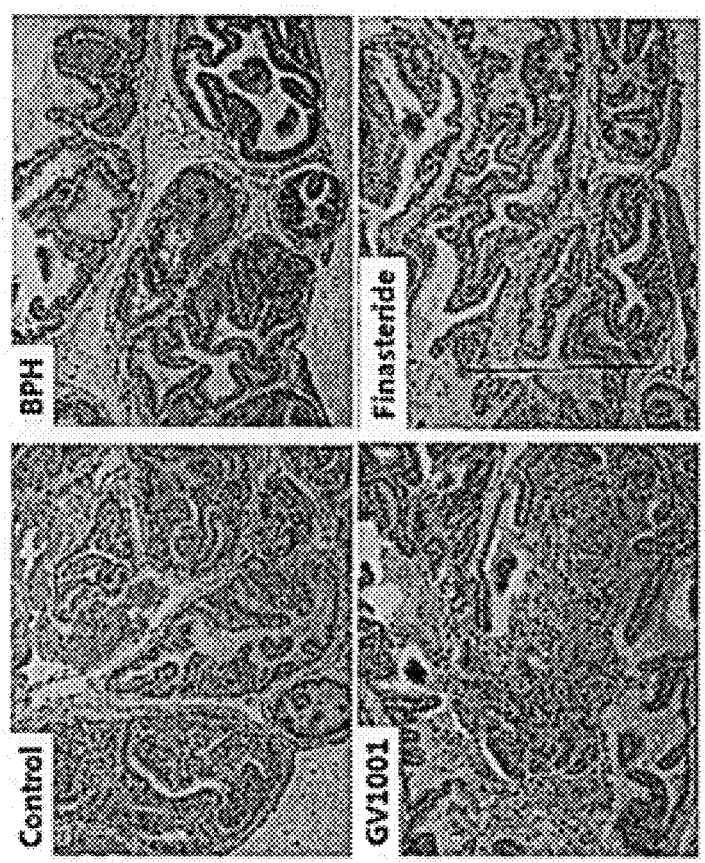
FIG. 10 represents an immunostaining photograph which shows the effect of PEP1 to the expression of Ki67 (MK67), which is increased in BPH induced model when BPH is induced.

Inducing BPH increases PCNA (proliferating cell nuclear antigen, compulsory protein for replication) and Ki67 (MK167, compulsory protein for proliferation of cell) in prostate tissues. Based on this, a test is done to measure the effectiveness of PEP1 to inhibiting PCNA and Ki67 expression in BPH induced mouse model. PCNA was measured by using 2D-gel electrophoresis with protein of the extracted from prostate tissue cells, and Ki67 was measured by immunostain method to detect expression level in tissue. As a result, the expression of PCNA and Ki67, which were increased in prostate tissue of BPH induced animal, were decreased by treatment of PEP1 (see FIG. 9 and FIG. 10). Therefore, PEP1 inhibits the BPH inducing factors and it can be effective to treating and improving BPH.

4) Measuring the Change of Tissue Related to Inducing BPH

Figure 11:
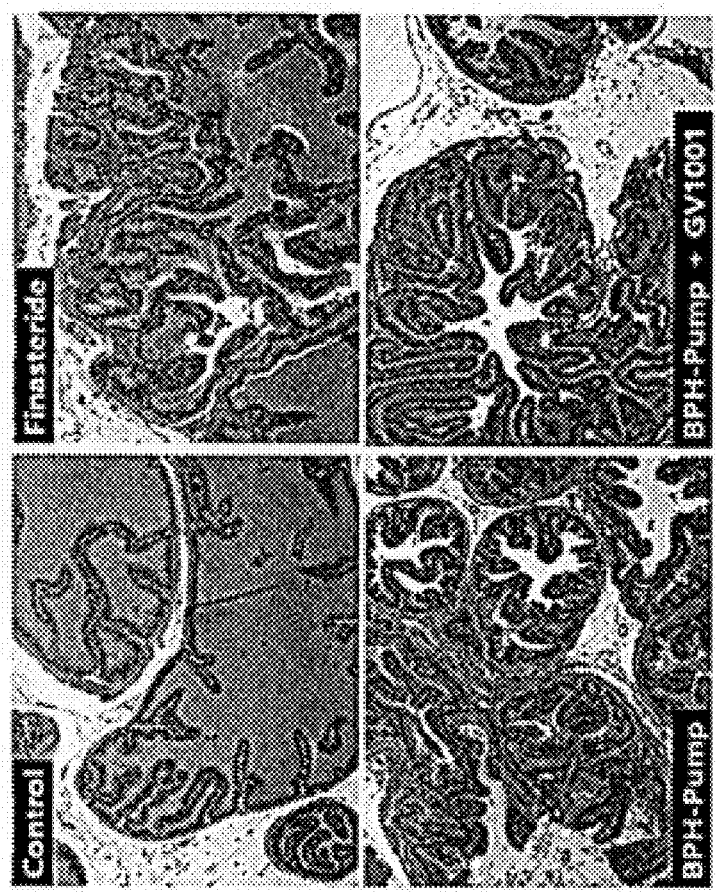
FIG. 11 represents a photograph of the results, which show the effect of PEP1 to cells related to BPH tissues in the experiment of BPH animal models by H&E stain method.
Figure 12:
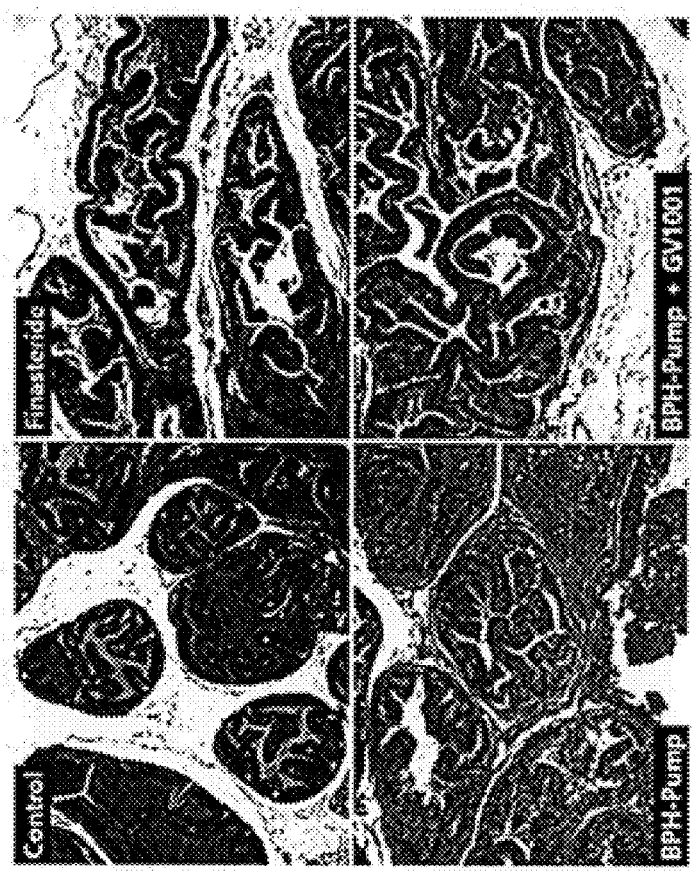
FIG. 12 represents a photograph of the results, which show the effect of PEP1 to cells related to BPH tissue in the experiment of BPH animal models by Masson's trichrome stain method.

It is known that BPH was induced by abnormal proliferation of stromal cell and epithelial cell which consist the prostate glands. Based on this, for detecting that PEP1 causes the changes in the prostate tissue of the BPH induced animal model, a histological analysis was done to BPH induced animal model. H&E staining method was used to detect the changes in general tissue and Masson's trichrome Staining method was used to measure the level of inflammatory reaction and to detect the shape of nuclear more clearly. For the result, it was shown that the epithelial layer of the BPH induced group was thicker than that of control group, but, in the group of treating PEP1, it was shown that the epithelial layer was arranged in regular order like that of control group and that the thickness of the epithelium was less thick than that of the BPH induced group (see FIGS. 11 and 12). Therefore, PEP1 can be effective for to restoring the changes of the BPH induced tissue and turning the tissue to the normal tissue, which does not show BPH.

5) Measuring the Changes of BPH Related Organs

Figure 13:
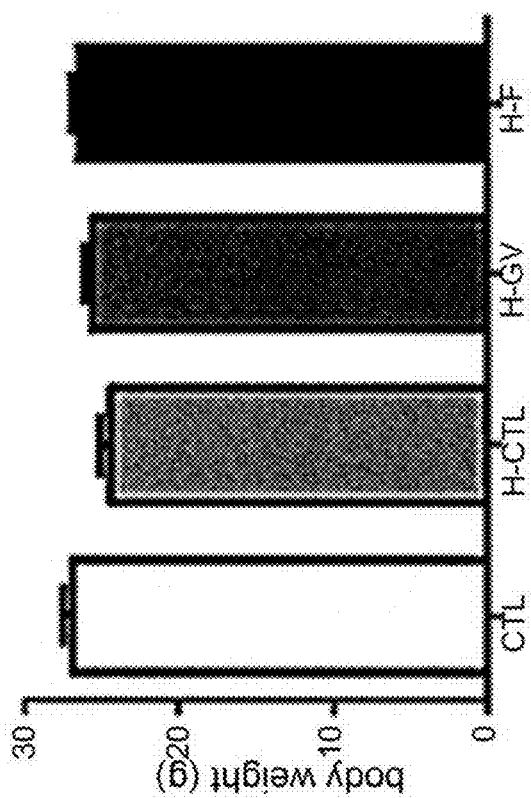
FIG. 13 represents a graph which shows the change of body weights of the animals in the experiment for measuring the effect of PEP1 in BPH animal model.
Figure 14:
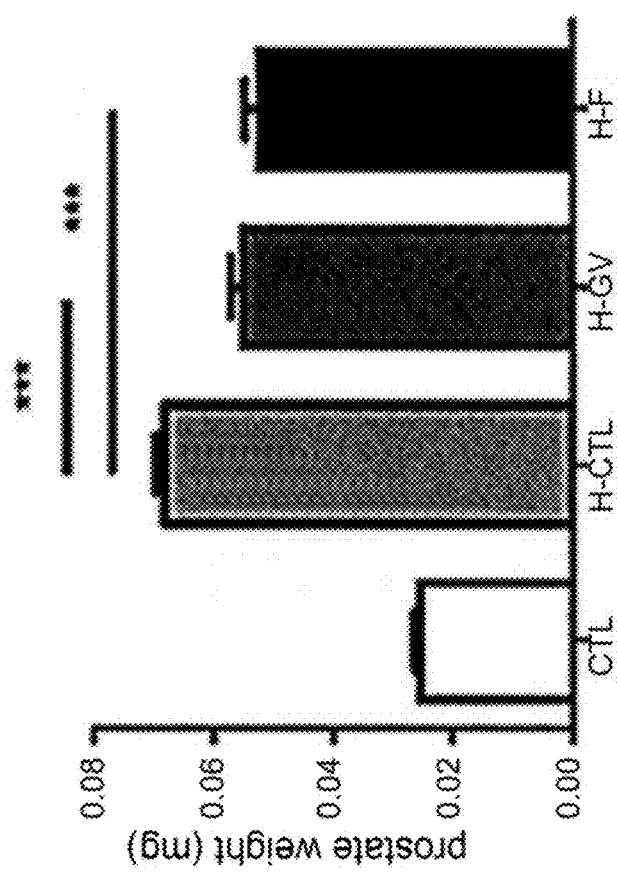
FIG. 14 represents a graph which shows the change of prostate weights of the animals models in the experiment for measuring the effect of PEP1 in BPH animal model.
Figure 15:
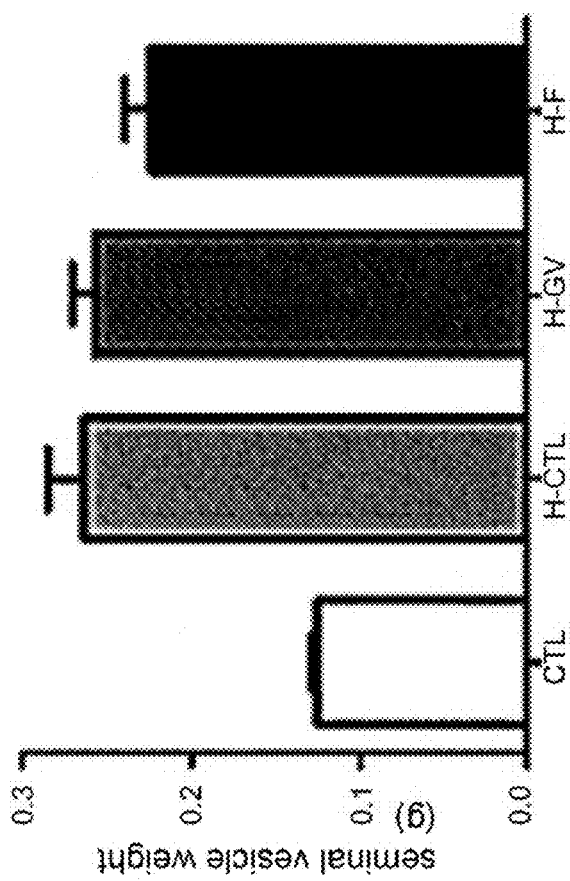
FIG. 15 represents a graph which shows the change of seminal vesicle weights of the animals in the experiment for measuring the effect of PEP1 in BPH animal model.

BPH can be detected by the changes of the weights of prostate and seminal vesicle. Based on this, for detecting the effect of PEP1 to the weights of prostate and seminal vesicle which directly show the BPH related symptoms, body weight, prostate weight and seminal vesicles weight were measured in BPH induced animal model. The results of the measurement are shown in Table 5 by group as a graph (see FIGS. 13, 14 and 15). The change of the overall body weight was not shown, but it was shown that the prostate weight in PEP1 treated group was significantly decreased as compared with the result of hormone treated group and the decrease of the weight in PEP1 treated group was comparable to the result of the group of administering finasteride, which was known as a drug for BPH treatment, and so it is confirmed that the decrease in PEP1 treated group is significant. For seminal vesicle, the seminal vesicle weight of the PEP1 treated group was less than that of the hormone treated group. Therefore, PEP1 can be effective for decreasing significantly the weight of organs having symptom of BPH.

In all examples above, through the experimental in BPH induced animal model in vitro and in vivo, it is shown that PEP1 has good treatment effect to the BPH related inducing factors, the hormone receptors, and the substantive reproductive organs. Therefore, it is considered that PEP1 is effective for treating, improving and preventing BPH, and there is a high likelihood of developing PEP1 into a composition for BPH treatment and a method for treating BPH.

Sequence List Free Text

Whole telomerase sequence 1132 aa

What is claimed is:

1. A method for treating or preventing benign prostatic hyperplasia (BPH) comprising administering to a subject known to have benign prostatic hyperplasia the isolated peptide of SEQ ID NO: 1.

2. The method according to claim 1, wherein the peptide is administered in a single dose at a concentration of 0.001 to 10 mg/kg body weight.

3. The method according to claim 1, wherein the peptide is administrated in a single dose at a concentration of 0.005 to 0.05 mg/kg body weight.

4. The method according to claim 1, wherein the peptide is administered 1 to 3 times a day.

5. The method of claim 1, wherein the peptide is administered at a daily dose of 0.001 to 10 mg/kg body weight.

6. The method of claim 5, wherein the peptide is administered 1 to 3 times daily.

7. A method for treating or preventing benign prostatic hyperplasia (BPH) comprising administering to a subject known to have benign prostatic hyperplasia a composition comprising the isolated peptide of SEQ ID NO:1.

8. The method according to claim 7, wherein the composition comprises an additive selected from the group consisting of diluents, excipients, lubricants, binders, disintegrants, buffers, dispersants, surfactants, coloring agents, aromatics, and sweeteners.

9. The method according to claim 7, wherein the composition is administered through a rectal, transdermal, intravenous, intramuscular, intraperitoneal, in the bone marrow, epidural, or subcutaneous route.

10. The method according to claim 7, wherein the composition comprises 0.01 g/L to 1 kg/L of the isolated peptide.

11. The method of claim 7, wherein the peptide is administered in a single dose at a concentration of 0.001 to 10 mg/kg body weight.

12. The method of claim 7, wherein the peptide is administered in a single dose at a concentration of 0.005 to 0.05 mg/kg body weight.

13. The method according to claim 7, wherein the composition comprises 0.56 mg of the isolated peptide.

14. The method according to claim 7, wherein the peptide is administered 1 to 3 times a day.

15. The method of claim 7, wherein the peptide is administered at a daily dose of 0.001 to 10 mg/kg body weight.

16. The method of claim 15, wherein the peptide is administered 1 to 3 times daily.

17. The method according to claim 7, wherein the composition is administered every 2 weeks for a total period of 12 weeks treatment, wherein the isolated peptide is administered each time at concentration of 4 nmol/kg of body weight.

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95
```

```
Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
        130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
```

-continued

```
            515                 520                 525
Val Pro Ala Glu His Arg Leu Arg Glu Ile Leu Ala Lys Phe
    530                 535                 540
Leu His Trp Leu Met Ser Val Tyr Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
    610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
    770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
        835                 840                 845
Met Glu Asn Lys Leu Phe Ala Gly Ile Arg Arg Asp Gly Leu Leu Leu
    850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
            900                 905                 910
Ala Leu Gly Gly Thr Ala Phe Val Gln Met Pro Ala His Gly Leu Phe
        915                 920                 925
Pro Trp Cys Gly Leu Leu Leu Asp Thr Arg Thr Leu Glu Val Gln Ser
    930                 935                 940
```

-continued

```
Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                1005

Ala Tyr  Arg Phe His Ala Cys  Val Leu Gln Leu Pro  Phe His Gln
    1010                1015                1020

Gln Val  Trp Lys Asn Pro Thr  Phe Phe Leu Arg Val  Ile Ser Asp
    1025                1030                1035

Thr Ala  Ser Leu Cys Tyr Ser  Ile Leu Lys Ala Lys  Asn Ala Gly
    1040                1045                1050

Met Ser  Leu Gly Ala Lys Gly  Ala Ala Gly Pro Leu  Pro Ser Glu
    1055                1060                1065

Ala Val  Gln Trp Leu Cys His  Gln Ala Phe Leu Leu  Lys Leu Thr
    1070                1075                1080

Arg His  Arg Val Thr Tyr Val  Pro Leu Leu Gly Ser  Leu Arg Thr
    1085                1090                1095

Ala Gln  Thr Gln Leu Ser Arg  Lys Leu Pro Gly Thr  Thr Leu Thr
    1100                1105                1110

Ala Leu  Glu Ala Ala Ala Asn  Pro Ala Leu Pro Ser  Asp Phe Lys
    1115                1120                1125

Thr Ile  Leu Asp
    1130
```